United States Patent
Pang et al.

(10) Patent No.: US 8,373,748 B2
(45) Date of Patent: Feb. 12, 2013

(54) AUTOMATIC ENDOSCOPE RECOGNITION AND SELECTION OF IMAGE PROCESSING AND DISPLAY SETTINGS

(75) Inventors: Chien Mien Pang, San Jose, CA (US); Yangpeng Ng, Santa Clara, CA (US); William H. L. Chang, Milpitas, CA (US); Emmet J. McCarthy, Gilroy, CA (US); Konstantin Y. Zak, San Jose, CA (US)

(73) Assignee: Stryker Corporation, Kalamazoo, MI (US)

(*) Notice: Subject to any disclaimer, the term of this patent is extended or adjusted under 35 U.S.C. 154(b) by 1627 days.

(21) Appl. No.: 11/304,916

(22) Filed: Dec. 14, 2005

(65) Prior Publication Data

US 2007/0132839 A1  Jun. 14, 2007

(51) Int. Cl.
*H04N 7/18* (2006.01)
(52) U.S. Cl. ............................................. 348/72; 348/65
(58) Field of Classification Search .................... 348/45, 348/72, 65; 600/101, 109, 112, 122, 119
See application file for complete search history.

(56) References Cited

U.S. PATENT DOCUMENTS

| | | | | |
|---|---|---|---|---|
| 4,910,590 A | * | 3/1990 | Gillies et al. ..................... | 348/65 |
| 5,475,420 A | * | 12/1995 | Buchin ............................ | 348/72 |
| 5,506,912 A | * | 4/1996 | Nagasaki et al. ............. | 382/103 |
| 5,589,874 A | * | 12/1996 | Buchin ............................ | 348/72 |
| 6,092,722 A | | 7/2000 | Heinrichs et al. | |
| 6,364,827 B1 | | 4/2002 | Irion et al. | |
| 7,136,098 B1 | * | 11/2006 | Burnett et al. ............. | 348/230.1 |
| 7,258,663 B2 | * | 8/2007 | Doguchi et al. ............... | 600/109 |
| 7,450,151 B2 | * | 11/2008 | Kaneko ............................ | 348/72 |
| 7,855,727 B2 | * | 12/2010 | Adler et al. ..................... | 348/65 |
| 2002/0101507 A1 | * | 8/2002 | Saito et al. ...................... | 348/65 |
| 2002/0196334 A1 | * | 12/2002 | Saito et al. ...................... | 348/65 |
| 2002/0196335 A1 | * | 12/2002 | Ozawa ............................ | 348/70 |
| 2003/0025789 A1 | | 2/2003 | Saito et al. | |
| 2003/0030722 A1 | * | 2/2003 | Ozawa et al. ................... | 348/71 |
| 2003/0076411 A1 | * | 4/2003 | Iida et al. ........................ | 348/65 |
| 2004/0030221 A1 | | 2/2004 | Ogawa | |
| 2004/0218060 A1 | * | 11/2004 | Egashira ..................... | 348/222.1 |

(Continued)

FOREIGN PATENT DOCUMENTS

| EP | 1484002 A | 12/2004 |
|---|---|---|
| JP | 11-500648 | 1/1999 |

(Continued)

OTHER PUBLICATIONS

PCT Notification of Transmittal of International Preliminary Examination Report for PCT Counterpart Application No. PCT/US2006/047734 Containing International Preliminary Examination, 8 pgs. (Jun. 26, 2008).

(Continued)

*Primary Examiner* — Tuan Ho
*Assistant Examiner* — Selam Gebriel
(74) *Attorney, Agent, or Firm* — Blakely, Sokoloff, Taylor & Zafman LLP

(57) ABSTRACT

A control unit is connected to an endoscopic video camera, which is connected to an endoscope. Image data representing an image is received by the control unit from the video camera. Based on a characteristic of the received image which is indicative of a physical characteristic of the endoscope, the endoscope is recognized and/or and the value of a parameter for processing or display of images acquired by the camera is then automatically selected.

16 Claims, 4 Drawing Sheets

U.S. PATENT DOCUMENTS

| | | | |
|---|---|---|---|
| 2005/0020879 A1* | 1/2005 | Suzuki | 600/118 |
| 2005/0078175 A1* | 4/2005 | Kaneko | 348/65 |
| 2005/0157168 A1* | 7/2005 | Kaneko | 348/72 |
| 2005/0231591 A1* | 10/2005 | Abe | 348/65 |
| 2007/0002134 A1* | 1/2007 | Ishihara et al. | 348/65 |
| 2008/0021272 A1* | 1/2008 | Doguchi et al. | 600/109 |

FOREIGN PATENT DOCUMENTS

| | | |
|---|---|---|
| JP | 2001 070240 A | 3/2001 |
| JP | 2001-70241 | 3/2001 |
| JP | 2003-334163 | 11/2003 |
| JP | 2004-33487 | 2/2004 |
| KR | 10-2004-0049837 | 6/2004 |
| WO | WO 97/15229 A1 | 5/1997 |
| WO | WO 03/010967 A1 | 2/2003 |

OTHER PUBLICATIONS

PCT Notification of Transmittal of the International Search Report and the Written Opinion of the International Searching Authority or the Declaration for PCT Counterpart Application No. PCT/US2006/047734 Containing International Search Report, 11 pgs. (May 30, 2007).

First Office Action for counterpart Chinese patent application No. 200680047454.8, dated Jan. 22, 2010, 9 pages.

First Examination Report for counterpart European patent application No. 06845432.1, dated Jun. 6, 2010, 3 pages.

First Office Action for counterpart Korean patent application No. 10-2008-7015834, dated Jan. 20, 2011, 7 pages.

Second Office Action for counterpart Chinese patent application No. 200680047454.8, 7 pages.

Office Action for counterpart European patent application No. 06845432.1, dated Mar. 3, 2011, 3 pages.

Third Office Action for counterpart Chinese patent application No. 200680047454.8, mailed Apr. 28, 2012, 9 pages.

Office Action for counterpart European patent application No. 06845432.1, mailed Mar. 6, 2012, 3 pages.

Examiner's First Report for counterpart Australian patent application No. 2006326386, dated Nov. 30, 2011, 2 pages.

Office Action for counterpart Japanese patent application No. 2008-545812, mailed Nov. 22, 2011, 4 pages.

* cited by examiner

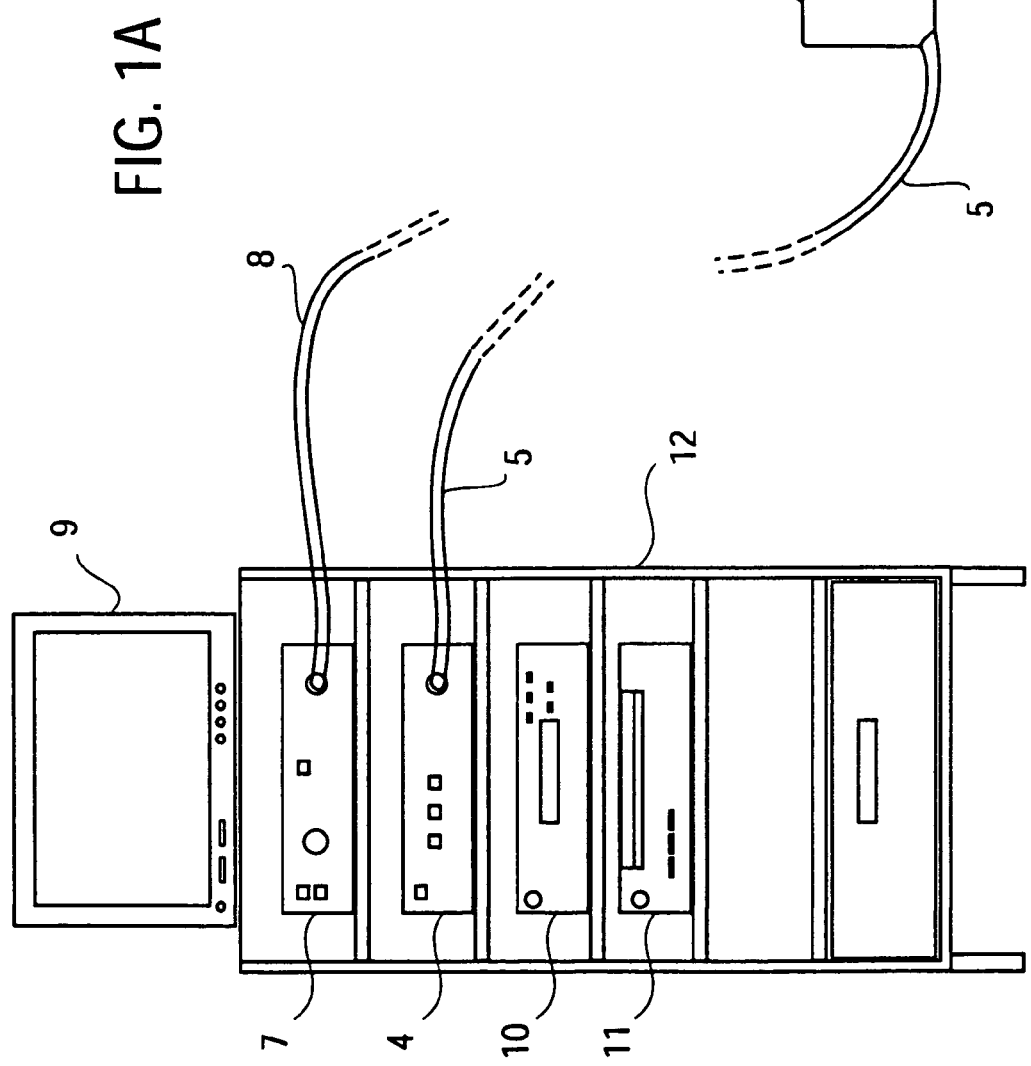

AUTOMATIC ENDOSCOPE RECOGNITION AND SELECTION OF IMAGE PROCESSING AND DISPLAY SETTINGS

FIELD OF THE INVENTION

At least one embodiment of the present invention pertains to endoscopic imaging system. More particularly, the invention relates to a technique for automatically identifying an endoscope that is coupled to an endoscopic video camera and for automatically selecting one or more settings for the display or processing of images thereby acquired.

BACKGROUND

Endoscopy in the medical field allows internal features of a patient's body to be viewed without the use of traditional, fully-invasive surgery. A basic tool of endoscopy is the endoscope (or "scope"). During an endoscopic medical procedure, one end of the scope is inserted into the body of a patient while the other end is typically connected to a video camera. The camera generates image data based on light received through the scope, and the image data is used to display real-time video images of the interior of the body on a display device.

The various types of scopes include flexible scopes such as commonly used in, e.g., gastroenterology, rigid scopes such as commonly used in, e.g., laparoscopy and arthroscopy, and semi-rigid scopes such as commonly used in, e.g., urology. Endoscopes are designed with various different physical and functional characteristics (length, diameter, type of optics, magnification, materials, degree of flexibility, etc.) to best suit their intended uses.

Since different types of endoscopic medical procedures are performed under different conditions, the camera settings tend to be dependent upon the type of procedure being performed. For example, in laparoscopy, more light is generally needed, because the abdominal cavity is so large. However, during arthroscopic shoulder surgery, too much light can produce reflection, making it difficult for the surgeon to see. Parameters whose settings may vary according to the procedure being performed may include, for example: video gain levels, enhancement level, camera shutter speed, gamma level, and others.

One problem with existing endoscopy systems is that it is inconvenient and time-consuming for medical personnel to have to determine and manually set the camera settings that are most appropriate for the procedure to be performed. Doing so may involve a trial and error process, which does not necessarily result in the most optimal settings being selected for the procedure.

SUMMARY OF THE INVENTION

The present invention includes a method that comprises receiving image data representing an image from a video camera coupled to an endoscope, and automatically selecting a value for a parameter for processing or display of images acquired by the video camera, based on a characteristic of the image which is dependent upon a physical characteristic of the endoscope.

Another aspect of the invention is a method that comprises receiving image data representing an image from a video camera coupled to an endoscope, and automatically recognizing the endoscope based on the characteristic of the image which is dependent on a physical characteristic of the endoscope.

The invention further includes a system and apparatus to perform such methods.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which:

FIG. 1A and 1B collectively illustrate an endoscopic medical imaging system;

DETAILED DESCRIPTION

A method and apparatus are described for automatically identifying an endoscope that is coupled to an endoscopic video camera and for automatically selecting one or more settings for the display or processing of images thereby acquired.

References in this specification to "an embodiment", "one embodiment", or the like, mean that the particular feature, structure or characteristic being described is included in at least one embodiment of the present invention. Occurrences of such phrases in this specification do not necessarily all refer to the same embodiment.

The image from an endoscopic video camera is commonly (though not always) circular when displayed on a monitor, due to the physical construction of the scope, depending on the magnification of the scope and/or the coupler which connects the scope to the camera. (Typically, a scope either has a built-in coupler or is designed to be used with a particular type of external coupler.) The available display area outside the circular image is normally black. The diameter of the image relative to the total available display area (i.e., frame size) depends on the magnification of the scope and/or the magnification of the coupler (if any), which in turn depends on the particular optics within the scope and the coupler. For example, laparoscopes, arthroscopes, cystoscopes, and hysteroscopes typically have different magnifications from each other, which results in different image sizes on the monitor.

Figure 2A:
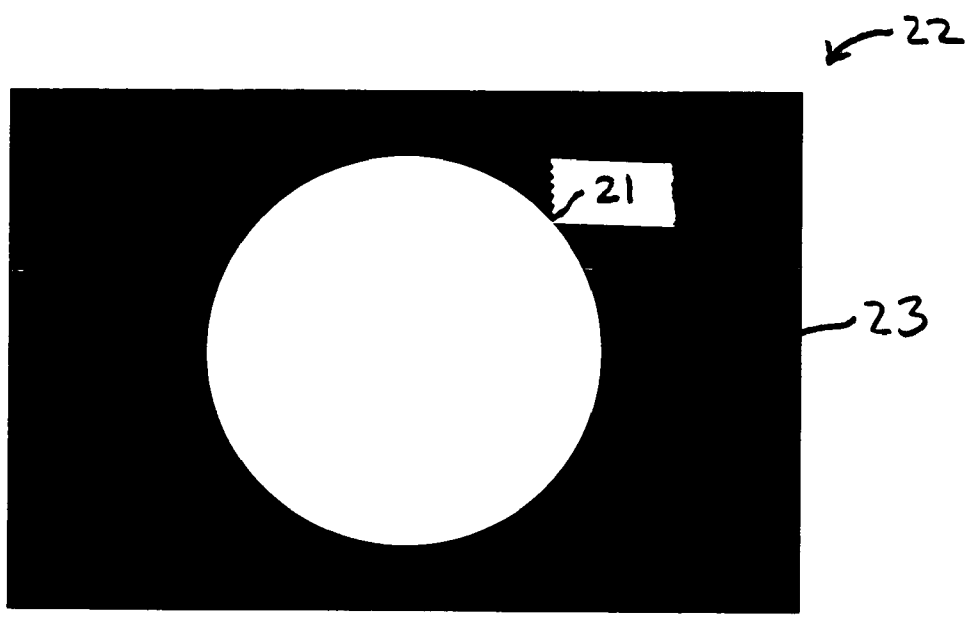
FIGS. 2A and 2B illustrate video frames resulting from two different endoscope/coupler combinations.
Figure 2B:
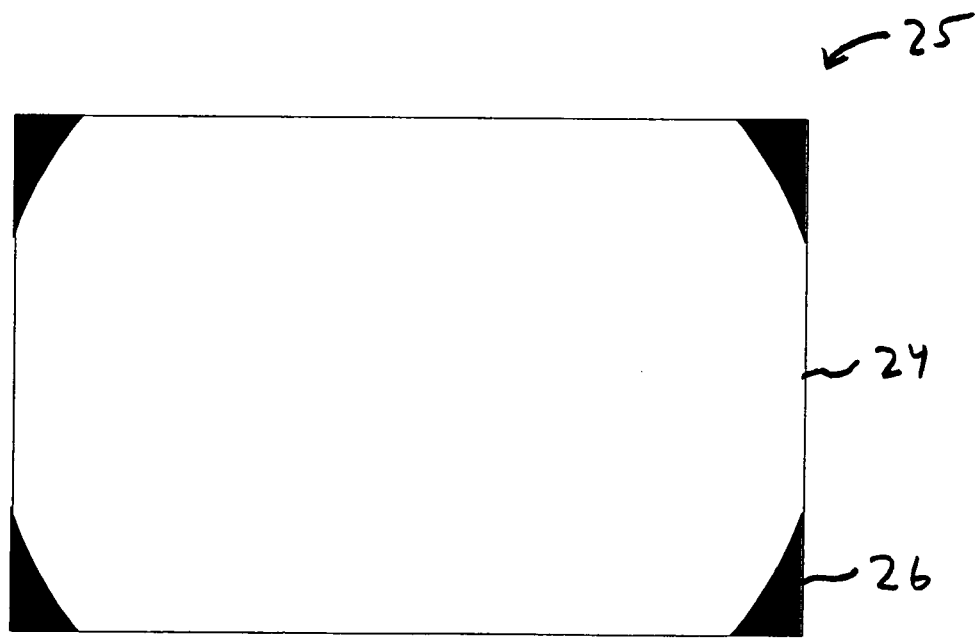

FIG. 2A shows an example of an image contained in a video frame generated by a video camera coupled to an endoscope. The circular image 21 is surrounded by black area 23 in the unused portion of the frame 22. FIG. 2B shows an example of an image which might be produced by a different scope and coupler which provide greater magnification than those associated with FIG. 2A. It can be seen that the diameter of the image 24 is larger, and the black area 26 correspondingly smaller, in frame 25 in FIG. 2B than the corresponding features of frame 22 in FIG. 2A.

Therefore, the actual image size relative to the total frame size can be considered an indication of the type (class) of scope that is attached to the camera, and therefore, of the type of procedure that is to be performed. The image size, or conversely, the amount of unused (black) display area outside the image, can therefore be used to infer physical characteristics of the scope (or the combination of scope and coupler) that is attached to the camera, such as its magnification (which depends on its optics). Therefore, the image size (or the amount of black space) can further be used as a basis to automatically recognize the type of scope being used (e.g., laparoscope, arthroscope, etc.) and/or to select the settings (values) for various image processing and display parameters which are most appropriate for that scope and/or the procedure being performed, since the type of scope is generally indicative of the type of procedure.

As described in greater detail below, therefore, a camera control unit (CCU) is connected to an endoscopic video camera, which is connected to a scope. In response to a start command or other similar signal before the beginning of an endoscopic procedure, the CCU counts the number of black pixels in each (horizontal) line of a video frame received from the camera and determines the minimum and maximum number of black pixels per line. These numbers are indicative of the diameter of the image (e.g., the larger the image, the smaller the minimum and maximum number of black pixels per line), which is indicative of the type of scope and coupler being used. For example, for laparoscopes the minimum number of black pixels per line is generally zero, since the image takes up an entire line for at least one line in the frame, as shown in FIG. 2B. A 10 mm diameter laparoscope generally has a maximum number of black pixels per line of zero (i.e., the image takes up the whole frame), while a 5 mm diameter laparoscope generally has a non-zero maximum number of black pixels per line, such as represented in FIG. 2B.

The minimum and/or maximum number of black pixels per line in a frame are therefore used to look up in a data structure and select the type of scope being used (e.g., laparoscope, arthroscope, etc.) and/or the appropriate values for various parameters used by the control unit for the processing or display of images. It is assumed that the data structure has been previously set up to contain the possible scope types and preferred values of the parameters, for multiple possible scope/coupler configurations. The values in the data structure may have been determined experimentally prior to being stored in the data structure (e.g., by the CCU manufacturer), well before this process is used.

In this way, the scope can be automatically recognized, and the preferred parameter settings for that combination of scope and coupler can be automatically identified and selected. This technique is advantageous in that no hardware modifications to the camera, coupler or scope are needed. This technique can be implemented entirely in software in a centralized device, such as a CCU. By avoiding the need for additional or more advanced hardware, this technique helps to reduce costs of the system and to provide a more reliable system.

In addition, or as an alternative, the CCU can send the input of the lookup operation (i.e., the minimum/maximum number of black pixels per line) or the looked up values to one or more other devices, such as a monitor or a digital video/image capture device, via any conventional communication link. This would allow the other device(s) to recognize the scope and coupler, or to determine an appropriate value for one or more parameters that depend on a physical characteristic of the scope and coupler. As another alternative, the CCU can send information about the recognized scope (e.g., information identifying the type of scope or other similar information) to the other device(s).

Note that for purposes of this document, the term "black" (e.g., regarding the number of black pixels) does not have to mean absolute black or the blackest value achievable by the equipment being used. Rather, it means that a specified minimum degree of blackness is present. Any reasonable threshold value can be used (e.g., for pixel color and/or intensity) to determine whether a particular pixel is black or not.

Refer now to FIGS. 1A and 1B, which collectively illustrate an example of an endoscopic medical imaging system in which this technique can be applied. FIG. 1A shows the image generation and display and support components of the system, while FIG. 1B illustrates the data acquisition components of the system. The data acquisition components include a scope 2, a video camera 3, and a coupler 6 connecting the scope 2 to the camera 3. The camera 3 acquires color video image data of internal features of a body through a system of lenses in the scope 2. Note that in some embodiments of the invention, the coupler 6 may be built into the scope 2, whereas in other embodiments the coupler 6 and scope 2 may be built as separate pieces. The technique introduced here is not limited to any particular configuration in this regard.

The image generation and display and support components of the system include a camera control unit (CCU) 4, a light source unit 7, a monitor 9, and various other devices 10 and 11, which are located on a mobile cart 12. The technique being introduced here for scope recognition and parameter value selection can be implemented within the CCU 4, as described further below. The other devices 10 and 11 may include any one or more of, for example: a video capture device, a printer, an RF cutter console to control an RF cutter during endoscopic surgery, and/or a shaver console to control a shaver during endoscopic surgery. Various other system configurations are also possible.

High-intensity light is provided to the scope 2 by the light source unit 7 through a flexible light conduit 8, such as fiber optic cable. Operation of the camera system and control of various image processing and display parameters can be controlled by or from the CCU 4. The camera 3 is coupled to the CCU 4 by a flexible transmission line 5. The transmission line 5 conveys power to the camera 3, conveys video image data from the camera 3 to the CCU 4, and conveys various control signals bi-directionally between the camera 3 and the CCU 4. Image data received by the CCU 4 from the camera 3 are processed and/or converted by the CCU 4 to video images that are displayed on the monitor 9 and, if desired, recorded by a video recorder and/or used to generate static images that can be printed by a printer.

Figure 3:
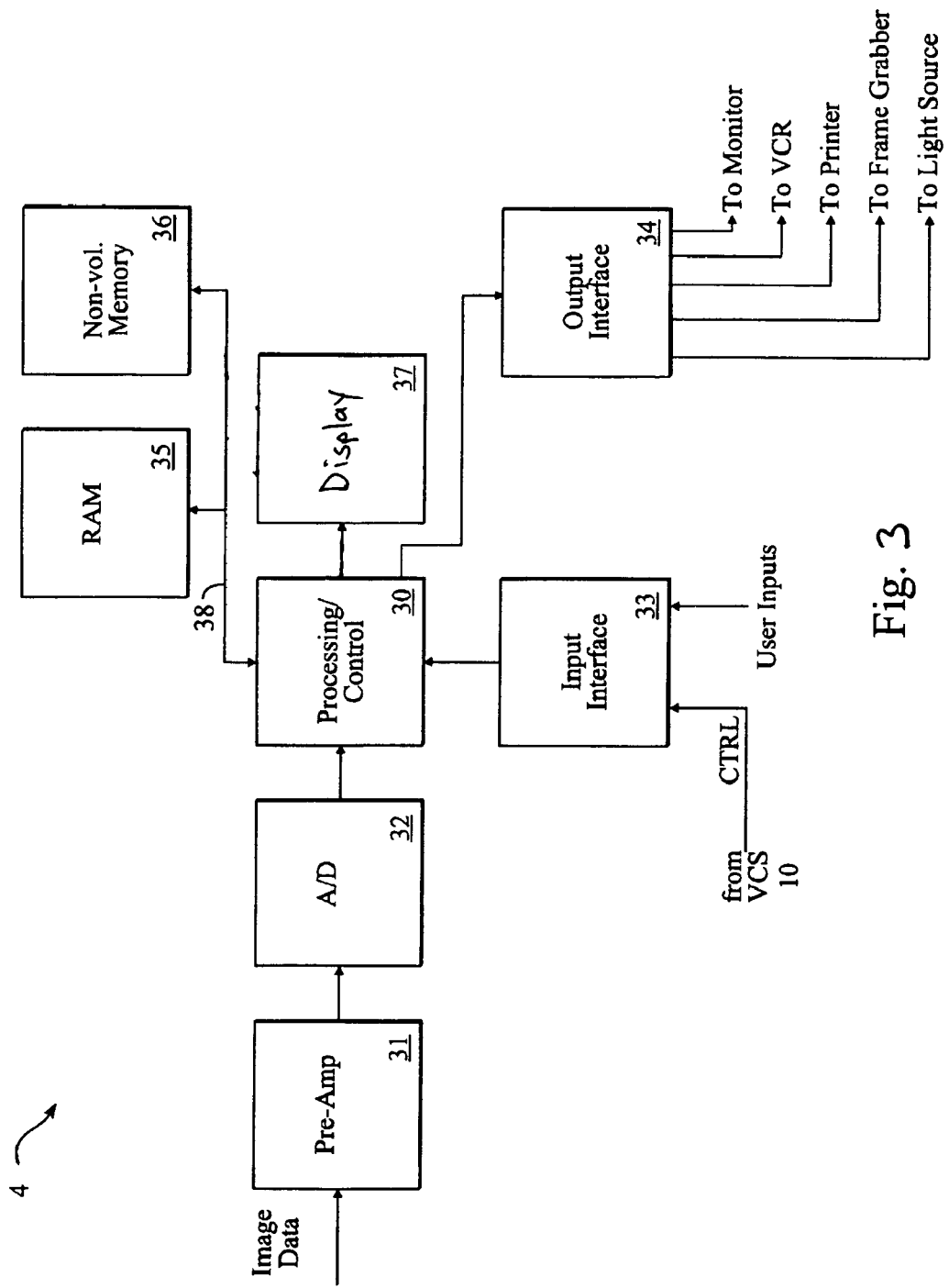
FIG. 3 is a block diagram showing an example of the architecture of the camera control unit (CCU)

FIG. 3 is a block diagram showing an example of the architecture of the CCU 4. In the illustrated embodiment, the CCU 4 includes a processing/control unit 30, a pre-amplification stage 31, an analog-to-digital (A/D) converter 32, an input interface 33, an output interface 34, a random access memory (RAM) 35, a non-volatile memory 36, and a display device 37 (e.g., a touch-screen LCD or the like).

Processing/control unit 30 controls the overall operation of the CCU 4 and performs signal processing, including functions commonly used in generating displayable video images. Also, in certain embodiments of the invention the processing/control unit 30 performs the automatic scope/coupler recognition and parameter value selection functionality being introduced here. Accordingly, processing/control unit 30 may be or may include, for example, a field programmable gate array (FPGA), a general- or special-purpose microprocessor, such as digital signal processor (DSP), an application specific integrated circuit (ASIC), or other appropriate device or combination of such devices. If processing/control unit 30 is designed to execute software, the software may be stored in RAM 35, in non-volatile memory 36, or both.

During operation of the camera system, image data (e.g., red (R), green (G) and blue (B) color signals) generated by the camera 3 is received (via transmission line 5) by pre-amplification stage 31, where the data undergoes amplification and appropriate signal conditioning. The amplified and conditioned data are then converted to digital form by A/D converters 32 and provided (e.g., as separate R, G and B digital signals) to processing/control unit 30. Of course, in an embodiment in which the camera 3 outputs digital data, the A/D converters 32 would be unnecessary. The processing/control unit 30 also receives the video vertical synchronization ("Vsync"), horizontal synchronization ("Hsync") and clock signals from the camera 3.

User inputs from manual controls on the CCU 4 and the camera 3 are input to input interface 33. In addition, control signals resulting from processed and recognized voice commands from an associated voice control system (VCS) may also be received by input interface 33. The input interface 33 then provides these inputs, after any appropriate buffering and/or signal conditioning, to processing/control unit 30, which processes the inputs accordingly.

In the illustrated embodiment, processing/control unit 30 provides video, graphical and/or text output directed to a local display device 37 on the CCU 4, and further provides various other outputs directed to the light source 7, external monitor 9, and other connected devices, via the output interface 34, which performs any appropriate buffering and/or signal conditioning.

Image data may be stored at various stages of processing in RAM 35, in non-volatile memory 36, in such other memory (not shown) as may be provided in the CCU 4, or in any combination thereof, all of which are coupled to processing/control unit 30 by a bus 38 or any other suitable type of connection. Non-volatile memory 36 may be any device suitable for storing relatively large amounts of data, such as: read only memory (ROM), which may be programmable and erasable; flash memory; an optical, magnetic or magneto-optical (MO) mass storage device; or a combination of such devices.

As noted above, the amount of black space in the image acquired by the camera is indicative of the diameter of the image, which is indicative of the magnification provided by the scope and/or the coupler. The magnification is indicative of the type of scope being used, which in turn is indicative of the type of procedure to be performed. Therefore, this characteristic of the image can be used to look up, in a data structure such as a lookup table, the type of scope being used and to look up and select appropriate values for various parameters used by the CCU 4 for the processing or display of images. The parameters may include, for example: maximum gain level, default enhancement level, maximum shutter level, shutter peak vs. average consideration, shutter speed, shutter area, gamma level, master pedestal, shading correction, knee point, knee slope, color gain levels, color bias levels, flexible scope filter activation, etc. The data structure has been previously set up to contain the various scope types likely to be encountered (e.g., laparoscope, arthroscope, etc.) and preferred values of the parameters, for multiple possible configurations and procedures. The minimum or maximum number of black pixels per line in a frame received from the camera can be used as the index value to look up the appropriate parameter values.

Figure 4:
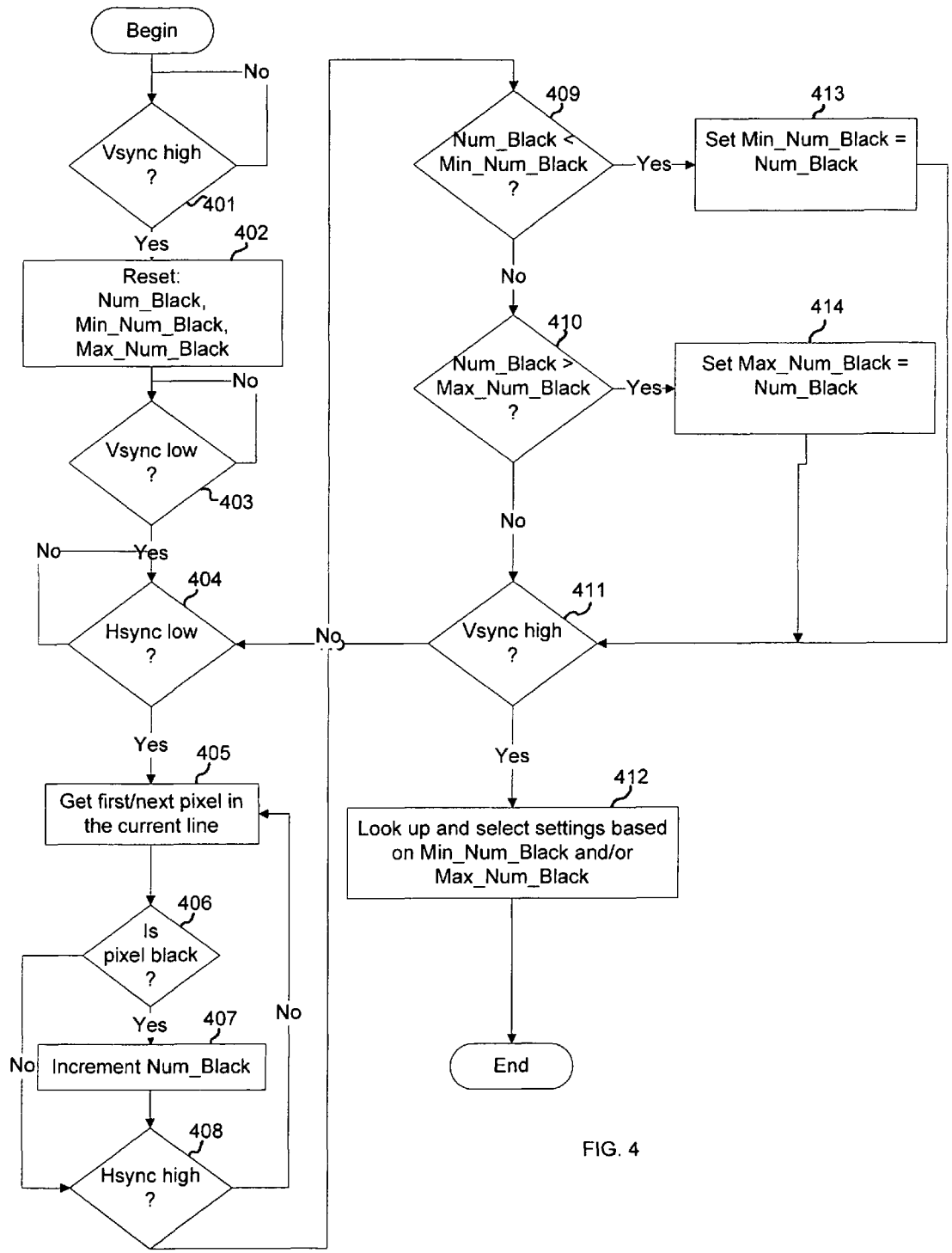
FIG. 4 shows a process for automatic endoscope recognition and parameter value selection.

FIG. 4 shows an example of a process for automatic scope recognition and parameter value selection, according to the technique being introduced here. The process may be performed in the CCU 4, for example. It is assumed that the process is initiated by a user input, either directly or indirectly; however, the remainder of the process is automatic. The user input may be applied at, for example, the camera 3 or the CCU 4.

The process uses the variables, Num_Black, Min_Num_Black, and Max_Num_Black. Min_Num_Black is a variable, the final value of which represents the minimum number of black pixels per line in the current frame. Max_Num_Black is a variable, the final value of which represents the maximum number of black pixels per line in the current frame. Num_Black is a temporary variable used in the process of determining Min_Num_Black and Max_Num_Black.

Once the initiating user input is received, the process waits at block 401 for the beginning of a new video frame to be received from the camera, which is indicated by the vertical synchronization ("Vsync") signal. Once Vsync goes high, the values of Num_Black, Min_Num_Black, and Max_Num_Black are reset at block 402. After these variables are reset, the process waits at block 403 for Vsync to go low. Once Vsync goes low, the process then waits at block 404 for the start of a new line within the current frame, which is indicated by the horizontal synchronization ("Hsync") signal going low.

Once Hsync goes low, at block 405 the process gets the first pixel in the current line. The process receives a pixel clock as input, so that a new pixel is clocked in after every clock cycle. The process then determines at block 406 whether the current pixel is black, based on any reasonable threshold to discriminate between "black" and "not black". In one embodiment, each pixel is a 10-bit hexadecimal value and a pixel is considered to be black if the two most significant bits of that value are zero (indicating a strong black presence). It is desirable that the camera and scope be aimed at something white during this process, to make it easier to distinguish pixels that are black from pixels that are not black.

If the current pixel is determined to be black at block 406, the variable NUM_Black is incremented by one at block 407, and the process then proceeds to block 408. If the pixel is determined not to be black at block 406, then the process proceeds from block 406 directly to block 408.

At block 408 the process determines whether Hsync has gone high, which would indicate the end of the current line has been reached. If Hsync has not gone high, the process loops back to block 405, by getting the next pixel in the current line and proceeding as described above.

If Hsync has gone high at block 408, then at this point the minimum and maximum number of black pixels in the frame (Min_Num_Black and Max_Num_Black, respectively) are updated, if appropriate. Specifically, at block 409, if NUM_Black is less than Min_Num_Black, then Min_Num_Black is set equal to NUM_Black at block 413. The process then continues to block 411. If NUM_Black is not less than Min_Num_Black, then the process determines at block 410 whether it NUM_Black is greater than Max_Num_Black. If NUM_Black is greater than Max_Num_Black, then the process sets Max_Num_Black equal to NUM_Black at block 414. The process then continues to block 411.

At block 411 the process determines whether Vsync is still low, which would indicate the end of the frame has not yet been reached. If Vsync is still low, the process loops back to block 404 and continues as described above (i.e., by processing the next line in the frame). If Vsync has gone high (meaning the entire frame has been processed), then the process uses Min_Num_Black or Max_Num_Black to look up the corresponding scope type and/or the corresponding parameter values in the above-mentioned data structure, which are then selected for use in further operation of the system. In other words, the scope types and parameter values in the data structure are all indexed according to Min_Num_Black or Max_Num_Black values in this embodiment.

Whether Min_Num_Black or Max_Num_Black is used to look up the settings in the data structure can be determined arbitrarily or as a matter of convenience. Alternatively, separate lookups can be performed using both Min_Num_Black and Max_Num_Black, as a way to verify the accuracy of the result of this process. For example, if the lookup using Max_Num_Black produces the same or similar result as the lookup using Max_Num_Black (e.g., within some level of tolerance), the result is deemed to be correct. If not, an error signal may be output to the user, prompting the user to manually select the parameter settings or at least to verify that the settings are correct.

In addition, or as an alternative, the CCU 4 can send the looked up values or the input to the lookup operation (i.e., Min_Num_Black or Max_Num_Black) to one or more other devices, such as a monitor or a digital video/image capture device, which can be local or remote to the CCU 4, to allow the other device(s) to recognize the scope, or to determine an appropriate value for one or more parameters that depend on a physical characteristic of the scope. The transmitted information can be sent via any conventional communication link, which can be a wired link or a wireless link. As another alternative, the CCU 4 can send information about the recognized scope (e.g., information identifying the scope type or other similar information) to the other device(s). For example, the CCU 4 might send information to another device informing the other device that the scope is a 5 mm laparoscope, as opposed to a 10 mm laparoscope or an arthroscope, hysteroscope, etc.

Thus, a method and apparatus have been described for automatically identifying an endoscope that is coupled to an endoscopic video camera and for automatically selecting one or more settings for the display or processing of images thereby acquired.

The term "logic", as used herein, can include, for example, hardwired circuitry, programmable circuitry, software, or any combination thereof. Software to implement the technique introduced here may be stored on a machine-readable medium. A "machine-accessible medium", as the term is used herein, includes any mechanism that provides (i.e., stores and/or transmits) information in a form accessible by a machine (e.g., a computer, network device, personal digital assistant (PDA), manufacturing tool, any device with a set of one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method comprising:
   receiving image data representing an image from a video camera coupled to an endoscope;
   automatically recognizing the type of endoscope being used based on a minimum or maximum number of black pixels per line; and
   automatically selecting a value for a parameter for processing or display of images acquired by the video camera, the selecting based on the minimum or maximum number of black pixels per line in the image data acquired by the video camera, wherein the number of black pixels per line is dependent upon a physical characteristic of the endoscope.

2. The method as recited in claim 1, wherein the physical characteristic of the endoscope comprises optics in the endoscope.

3. The method as recited in claim 1, wherein the physical characteristic of the endoscope is a magnification of the endoscope.

4. The method as recited in claim 1, wherein the image is a video frame.

5. An apparatus comprising:
   an input interface through which to receive image data generated by a video camera coupled to an endoscope, the image data representing a video frame;
   logic to automatically recognize the type of endoscope being used based on a minimum or maximum number of black pixels per line in the video frame; and
   logic to automatically select a value for a parameter, based on the minimum or maximum number of black pixels per line in the video frame acquired by the video camera, wherein the number of black pixels per line is dependent on a physical characteristic of the endoscope.

6. The apparatus as recited in claim 5, wherein the parameter is a parameter for processing or display of images acquired by the video camera.

7. The apparatus as recited in claim 5, wherein the parameter corresponds to a class of endoscope to which the endoscope belongs.

8. The apparatus as recited in claim 5, wherein the physical characteristic of the endoscope comprises optics of the endoscope.

9. The apparatus as recited in claim 5, wherein the physical characteristic of the endoscope comprises a magnification of the endoscope.

10. The apparatus as recited in claim 5, wherein the physical characteristic of the endoscope comprises a magnification of the endoscope, and wherein the parameter is a parameter for processing or display of images acquired by the video camera.

11. An apparatus comprising:
    a video input interface through which to receive image data from a video camera coupled to an endoscope, the image data representing a video frame;
    a memory to store the image data representing a video frame;
    logic to recognize the type of endoscope being used based on the minimum or maximum number of black pixels per line; and
    logic to identify a characteristic of the endoscope based on a minimum or maximum number of black pixels per line in the video frame acquired by the video camera, wherein the number of black pixels per line is dependent upon the characteristic of the endoscope.

12. The apparatus as recited in claim 11, wherein the characteristic of the endoscope comprises a class of endoscope to which the endoscope belongs.

13. The apparatus as recited in claim 11, wherein the characteristic of the endoscope comprises a magnification of the endoscope.

14. The apparatus as recited in claim 11, further comprising:
    logic to transmit information identifying the recognized endoscope type to an external device.

15. The method as recited in claim 1, wherein the parameter for processing or display of images acquired by the video camera is a maximum gain level, default enhancement level, maximum shutter level, shutter peak vs. average consideration, shutter speed, shutter area, gamma level, master pedestal, shading correction, knee point, knee slope, color gain level, color bias level, or flexible scope filter activation.

16. The apparatus as recited in claim 6, wherein the parameter for processing or display of images acquired by the video camera is a maximum gain level, default enhancement level, maximum shutter level, shutter peak vs. average consideration, shutter speed, shutter area, gamma level, master pedestal, shading correction, knee point, knee slope, color gain level, color bias level, or flexible scope filter activation.

\* \* \* \* \*